US012673104B2

(12) United States Patent
Sanyal et al.

(10) Patent No.: US 12,673,104 B2
(45) Date of Patent: Jul. 7, 2026

(54) CLEAVABLE POLYMER DRUG CONJUGATES

(71) Applicant: RS ARASTIRMA EGITIM DANISMANLIK ILAC SANAYI TICARET ANONIM SIRKETI, Istanbul (TR)

(72) Inventors: Rana Sanyal, Istanbul (TR); Amitav Sanyal, Istanbul (TR); Mehmet Arslan, Istanbul (TR); Burcu Sumer Bolu, Istanbul (TR); Ozgul Gok, Istanbul (TR); Merve Karacivi, Istanbul (TR); Sadik Kaga, Istanbul (TR)

(73) Assignee: RS ARASTIRMA EGITIM DANISMANLIK ILAC SANAYI TICARET ANONIM SIRKETI, Istanbul (TR)

( * ) Notice: Subject to any disclaimer, the term of this patent is extended or adjusted under 35 U.S.C. 154(b) by 143 days.

(21) Appl. No.: 16/314,328

(22) PCT Filed: Jun. 15, 2017

(86) PCT No.: PCT/IB2017/053567
§ 371 (c)(1),
(2) Date: Dec. 28, 2018

(87) PCT Pub. No.: WO2018/002761
PCT Pub. Date: Jan. 4, 2018

(65) Prior Publication Data

US 2019/0321479 A1 Oct. 24, 2019

(30) Foreign Application Priority Data

Jun. 30, 2016 (GB) ..................................... 1611405

(51) Int. Cl.

| | |
|---|---|
| ***A61K 47/58*** | (2017.01) |
| ***A61K 47/10*** | (2017.01) |
| ***A61K 47/18*** | (2017.01) |
| ***A61K 47/32*** | (2006.01) |
| ***A61K 47/60*** | (2017.01) |
| ***A61K 47/65*** | (2017.01) |
| ***C08F 220/28*** | (2006.01) |
| *A61K 31/09* | (2006.01) |
| *A61K 31/337* | (2006.01) |
| *A61K 31/35* | (2006.01) |
| *A61K 31/4706* | (2006.01) |
| *A61K 31/506* | (2006.01) |
| *A61K 31/519* | (2006.01) |
| *A61K 45/06* | (2006.01) |
| *C08F 220/60* | (2006.01) |
| *C08F 222/10* | (2006.01) |

(52) U.S. Cl.
CPC .............. *A61K 47/32* (2013.01); *A61K 47/10* (2013.01); *A61K 47/183* (2013.01); *A61K 47/58* (2017.08); *A61K 47/60* (2017.08); *A61K 47/65* (2017.08); *C08F 220/286* (2020.02); *A61K 31/09* (2013.01); *A61K 31/337* (2013.01); *A61K 31/35* (2013.01); *A61K 31/4706* (2013.01); *A61K 31/506* (2013.01); *A61K 31/519* (2013.01); *A61K 45/06* (2013.01); *C08F 220/603* (2020.02); *C08F 222/1063* (2020.02)

(58) Field of Classification Search
CPC ......... A61K 47/58; A61K 47/65; A61K 47/60
See application file for complete search history.

(56) References Cited

U.S. PATENT DOCUMENTS

2015/0374663 A1* 12/2015 Benoit ............... A61K 47/6925
424/78.29

FOREIGN PATENT DOCUMENTS

WO WO 2007/028347 A2 3/2007
WO WO 2010/091650 A1 8/2010
WO WO-2015073579 A1 * 5/2015 ........... A61K 31/337

OTHER PUBLICATIONS

Chen et al. "Real-time monitoring of a controlled drug delivery system in vivo: construction of a near infrared fluorescence monomer conjugated with pH-responsive polymeric micelles" J. Mater. Chem. B, 2016, 4, 3377.*

Cai et al. "Functional 2-methylene-1,3-dioxepane terpolymer: a versatile platform to construct biodegradable polymeric prodrugs for intracellular drug delivery" Polym. Chem., 2014, 5, 4061 (Year: 2014).*

Fournier, "Tunable pH- and Temperature-Sensitive Copolymer Libraries by Reversible Addition-Fragmentation Chain Transfer Copolymerizations of Methacrylates", Macromolecules 2007, 40, Nov. 12, 2006, pp. 915-020.

Jones, "Thermoresponsive Copolymers of Methacrylic Acid and Poly(ethylene glycol) Methyl Ether Methacrylate", Department of Chemistry, McMaster University, Hamilton, Ontario, Canada, Aug. 16, 2005, pp. 1-10.

(Continued)

*Primary Examiner* — James W Rogers
(74) *Attorney, Agent, or Firm* — Lisa Mueller; Casimir Jones SC

(57) ABSTRACT

This invention relates to polymer drug conjugates comprising a (meth)acrylate based polymer backbone with at least two types of side chains wherein one of the side chains is a PEG chain and the other side chain comprises at least one therapeutic agent covalently bonded to a cleavable linker, methods of preparing said polymer-drug conjugates and their use for treatment of diseases such as cancer.

11 Claims, 1 Drawing Sheet

Specification includes a Sequence Listing.

(56) References Cited

OTHER PUBLICATIONS

Kopecek, "HPMA copolymer—anticancer drug conjugates: design, activity, and mechanism of action", European Journal of Pharmaceutics and Biopharmaceutics 50 (2000) 61-81, Jan. 22, 2000, pp. 1-21.
Krieg, "Dual hydrophilic polymers based on (meth)acrylic acid and poly(ethylene glycol)—synthesis and water uptake behavior", www.rsc.org/polymers, Polymer Chemistry, Jul. 8, 2010, pp. 1-8.
Kusch, "Characterization of copolymers of methacrylic acid with poly(ethylene glycol) methyl ether methacrylate macromonomers by analytical pyrolysis-gas chromatography/mass spectrometry (Py-GC/MS)", Journal of Analytical and Applied Pyrolysis (Mar. 2015); pp. 1-7.
Nuhn, "RAFT-polymerized poly(hexafluoroisopropyl methacrylate)s as precursors for functional water-soluble polymers", Polymer Chemistry Paper, Jan. 24, 2014, pp. 1-12.
Pei, "Triply Responsive Soft Matter Nanoparticles based on Poly[oligo(ethylene glycol) methyl ether methacrylate-block-3-phenylpropyl methacrylate] Copolymers", Polymer Chemistry Accepted Manuscript, Mar. 24, 2016, pp. 1-13.
Schmolke, "Poly(acrylic acid)-graft-poly(ethylene glycol) preparation and adsorption on polyelectrolyte multilayers (PEMs) for custom-made antiadhesive surfaces", Phys. Status Solidi A 208, No. 6, 1290-1300 (2011)/DOI 10.1002/pssa.201100002; May 11, 2011, pp. 1-11.
Seehuber, "Poly(acrylic acid)-Poly(ethylene glycol) Layers on Positively Charged Surface Coatings: Molecular Structure, Protein Resistance, and Application to Single Protein Deposition", Applied Physical Chemistry and Institute of Inorganic Chemistry, University of Heidelberg, 69120 Heidelberg, Germany, May 9, 2012 pp. 1-11.
Tan, "Room Temperature Synthesis of Poly(poly(ethylene glycol) methyl ether methacrylate)-based Diblock Copolymer Nano-objects via Photoinitiated Polymerization-Induced Self-Assembly (Photo—PISA)", Polymer Chemistry Accepted Manuscript, www.rsc.org/polymers, Feb. 24, 2016, pp. 1-25.

* cited by examiner

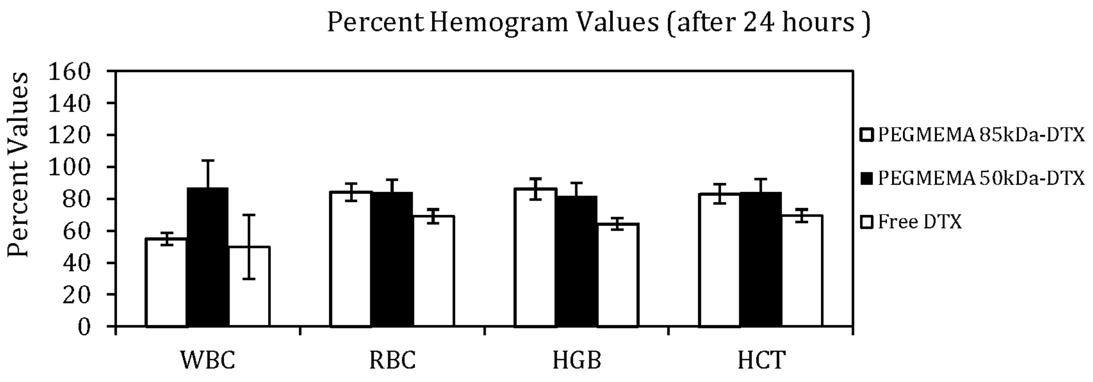
Percent Hemogram Values (after 24 hours )
Percent Values
160
140
120
100
80
60
40
20
0
WBC
RBC
HGB
HCT
PEGMEMA 85kDa-DTX
PEGMEMA 50kDa-DTX
Free DTX

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Phe Leu Gly
1


<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2
```

-continued

```
Ala Leu Ala Leu
1
```

CLEAVABLE POLYMER DRUG CONJUGATES

CROSS-REFERENCE TO RELATED APPLICATIONS

This application is a National Stage Entry of International Application No. PCT/IB2017/053567, filed on Jun. 15, 2017, which claims the benefit of United Kingdom Application No. 1611405.0, filed Jun. 30, 2016, the contents of each of which are herein incorporated by reference in its entirety.

This invention relates to polymer drug conjugates according to formula I, methods of preparing said polymer-drug conjugates and their use for treatment of diseases such as cancer.

BACKGROUND OF THE INVENTION

Chemotherapy agents used for treatment of cancer are mostly cytotoxic. These agents may accumulate in the tissues of the body in addition to the targeted area, which in turn causes lowered therapeutic benefit and undesired distribution of the drug throughout healthy body tissues. The uncontrolled distribution of these agents throughout the body causes severe side effects to the patient.

Due to distribution of the chemotherapy agents to the entire body including the healthy tissue, the amount of chemotherapy agent reaching the tumor tissue is very low despite the high overall toxicity caused by the given dose. This situation leads to low therapeutic benefit for the patient. Moreover, chemotherapy agents have low solubility which makes them difficult to formulate and administer to the patient.

In order to address the abovementioned problems, drug delivery systems, which can deliver the drug to targeted areas of the body, are developed. For example in some approaches of cancer treatment, these systems make use of the enhanced permeability and retention effect (EPR) which implies that drug carriers having high molecular weight and large hydrodynamic volume accumulate in solid tumors and this, in turn leads to passive targeting of the drug molecule to the tumor tissue and minimize the damage of the chemotherapy agents to healthy tissue.

TECHNICAL FIELD OF THE INVENTION

There are a number of polymers that can be used for preparing polymer-drug conjugates.

U.S. Pat. No. 6,310,039 disclose conjugates of transferrin, albumin and polyethylene glycol and cytostatic compounds such as doxorubicin, daunorubicin, epirubicin etc. In this document, the drug molecules are attached to the end groups of a polyethylene glycol polymer. One drawback of these systems is that they have limited functional groups for drug conjugation as a result they have a low drug percentage on the final drug polymer conjugate. Furthermore, aggregation is another phenomenon that is hard to deal with for this type of polymer drug conjugates.

For example, WO 1998/056424 discloses a polymer drug conjugate wherein dextrin forms the backbone of the polymer and the drug molecules are either directly or indirectly bound to the polymer backbone.

Another example is WO 2007/028347 that discloses a method for preparing a polymeric conjugate of the doxorubicine, which is an anti-cancer drug molecule. The document teaches use of N-(2-hydroxy propyl) methacrylamide (HPMA) monomer for formation of the polymer.

US 2003/0215395 discloses a cationic polymer such as poly(L-lycine), polyethylene imine and chitosan conjugated to a drug with a linker.

The above systems employ drug molecules attached to the polymer backbone via a linker aiming cleavage of the linker after the polymer-drug conjugate reaches its target tissue, thus releasing the drug molecule at the target site. However, the disadvantage of these systems is that the cleavable linker between the drug and the polymer cleaves in the blood stream and releases the drug molecule before it reaches its target tissue.

In light of the abovementioned state of the art, there is a need for a new polymer-drug conjugate, which is less toxic and has desirable pharmacokinetic profile.

Another object of the present invention is to provide a polymer-drug conjugate which addresses the problem of drug cleavage before the polymer drug conjugate reaches the targeted tissue.

The inventors have surprisingly found that a polymer-drug conjugate according to present invention has considerably higher circulation time, provides selective distribution of the active agent to the targeted tissues, has lower volume of distribution, lower clearance, and higher maximum concentration (Cmax) and higher total area under the curve (AUC total) values.

BRIEF DESCRIPTION OF THE INVENTION

Present invention relates to a polymer-drug conjugate for delivery of therapeutic agents comprising a (meth)acrylate based polymer backbone characterized in that the polymer comprises at least two types of side chains wherein one of the side chains is a PEG chain such as $COOCH_2CH_2(OCH_2CH_2)_nOR_3$ wherein n is a natural number between 1-200 and $R_3$ is selected from a group comprising H or $CH_3$ and the other side chain is comprising at least one therapeutic agent covalently bonded to a cleavable linker as shown in Formula I Formula I

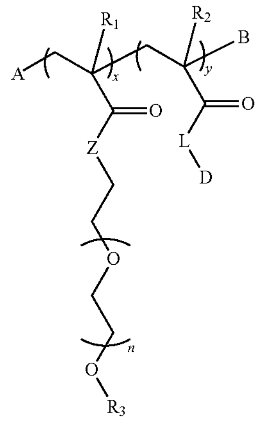

In other words, the invention relates to a polymer-drug conjugate of Formula I, wherein $R_1$ and $R_2$ are independently selected from H or $CH_3$ $R_3$ is selected from H or $CH_3$ x is a natural number between 1-140 y is a natural number between 1-40 n is a natural number between 1-200 and

L is a cleavable linker and
D is at least one therapeutic agent
Z is selected from —O or —NH
A is an end group that is optionally a polymerization initiator or a fragment thereof or A may be null
B is an end group that is optionally a polymerization initiator or a fragment thereof or B may be null The inventors have surprisingly found that in addition to overcoming the disadvantages of the prior art drug delivery systems comprising polymer-drug conjugates; the polymer of the present invention has reduced accumulation in the other organs due to the presence of biodegradable PEG side chains. This, in turn, provides a polymer-drug conjugate that has lower toxicity.

DETAILED DESCRIPTION OF THE INVENTION

The term "polymer-drug conjugate" refers to a polymeric structure having a therapeutic agent covalently attached to the polymer.

The terms "polymeric backbone" and "polymer backbone" can be used interchangeably and refer to a polymer chain having side chains or pendant groups. For example, a side chain may have an oligo ethylene glycol unit and a pendant group may be bearing one therapeutic agent or any other group that can be utilized to attach a therapeutic and/or diagnostic agent or a targeting group.

The term "acrylate" refers to derivatives of acrylic acids. These derivatives include the parent acid ($CH_2CHCO_2H$) and esters, thus the term "acrylate based" defines functional groups having any of the abovementioned acrylate derivatives.

The term "methacrylate" refers to derivatives of methacrylic acids. These derivatives include the parent acid ($CH_2C(CH_3)CO_2H$) and esters. Thus the term "methacrylate based" defines functional groups having any of the abovementioned methacrylate derivatives.

The term "(meth)acrylate" refers to the terms "acrylate" and "methacrylate". Thus, the term "(meth)acrylate" can be used interchangeably with "acrylate" and "methacrylate" and comprises all features of these terms as described above. The term "(meth)acrylate" should be construed to mean "methacrylate and/or acrylate"

Throughout the text, the term "the polymer-drug conjugate of the invention" should be construed to mean "a polymer-drug conjugate according to formula I" or "a polymer-drug conjugate of formula I" or "formula I" and these terms can be used interchangeably.

The term "PEG" refers to a polyether compound having the structure of $H—(O—CH_2—CH_2)n\text{-}OR_3$, n being a natural number between 1-200 and $R_3$ selected from H or $CH_3$. PEG is defined as an oligomer or polymer of ethylene oxide. The terms "PEG", "polyethylene glycol", "polyethylene oxide", "PEO", "polyoxyethylene" and "POE" refer to the same structure and may be used interchangeably within this text.

As shown by formula I the polymer-drug conjugate of the invention comprises PEG side chains. The side chains provide important physicochemical properties to the polymer-drug conjugate of the invention and leads to a polymer-drug conjugate that has better physicochemical properties in comparison to the conjugates that does not have said side chains.

As mentioned above "L" in formula I denotes a cleavable linker. The term "Cleavable linker" refers to a group that spatially separates drug or a targeting group from the carrier molecule. The terms "linker", "L" and "cleavable linker" refer to the same entity and can be used interchangeably.

Herein, the term "short peptide" should be construed to mean a peptide chain comprising 1-50 aminoacids, preferably 2-40 aminoacids and most preferably 2-30 aminoacids.

In one embodiment $R_1$=H, $R_2$=H, $R_3$=H; In another embodiment $R_1$=H, $R_2$=H, $R_3$=—$CH_3$; In another embodiment $R_1$=H, $R_2$=—$CH_3$, $R_3$=H; In another embodiment $R_1$=H, $R_2$=—$CH_3$, $R_3$=—$CH_3$; In another embodiment $R_1$=—$CH_3$, $R_2$=H, $R_3$=H; In another embodiment $R_1$=—$CH_3$, $R_2$=H, $R_3$=—$CH_3$; In another embodiment $R_1$=—$CH_3$, $R_2$=—$CH_3$, $R_3$=H; In another embodiment $R_1$=—$CH_3$, $R_2$=—$CH_3$, $R_3$=—$CH_3$.

The term "random copolymer" refers to a copolymer wherein the monomers forming the copolymer follow in any order. The term "block copolymer" refers to a copolymer wherein all of one type of monomer is grouped together and the all of the other type of monomers are grouped together. The polymer-drug conjugates of the invention can be in the form of block copolymer or random copolymers. The polymer-drug conjugates of the invention are in the form of random copolymer.

The linkers are cleavable so that the therapeutic agent can be released, for example, under reducing conditions, oxidizing conditions or by hydrolysis of an ester, amide, hydrazide, or similar linkage that forms the covalent bond between the linker and the therapeutic agent. Additionally, the type of linker may augment the selective cytotoxicity (and thus improve the therapeutic index) aspect by permitting selective release of the therapeutic agent adjacent to or inside the cell.

Said cleavable linker can be any hydrocarbon or substituted hydrocarbon based compound which is capable of dissociating under physiological conditions. In a preferred embodiment the linker can be selected from compounds that are cleaved under the acidic conditions of the tumor (such as any $C_1$-$C_{10}$ substituted hydrocarbon comprising an acetal or an ester functional group) or with the help of the overexpressed enzymes present in the intercellular or intracellular matrix of the tumor cells.

The linker can be any sort of entity capable of binding to both the polymer backbone and to the drug, such as, a poly(ethylene glycol), an amino acid, poly(amino acid) (e.g. a peptide or oligopeptide), or polypeptide (e.g. a protein), such that one end of it is capable of forming a covalent bond with the polymer backbone and the other end of it is capable of forming a covalent bond with the therapeutic agent. The linkers may also include short peptides with specific peptide sequences that are cathepsin B labile, such as Gly-Phe-Leu-Gly (SEQ ID NO: 1) also denoted as GFLG or Val-Cit or Phe-Lys or Val-Ala or Ala-Leu-Ala-Leu (SEQ ID NO: 2)

The linker can also be a $C_1$-$C_{10}$ hydrocarbon or a $C_1$-$C_{10}$ substituted or hetero substituted hydrocarbon such that it comprises a functional group that dissociates under physiological conditions, such as an acetal, ester, imine, amide, disulfide, carbonate, carbamate, hydrazone.

The term "$C_1$-$C_{10}$ hydrocarbon" refers to a hydrocarbon chain having 1 to 10 C atoms in the backbone.

The term "$C_1$-$C_{10}$ substituted hydrocarbon" refers to a hydrocarbon chain having 1 to 10 C atoms in the backbone wherein one or more of its hydrogen atoms replaced by atoms of groups of other elements such as alcohol, amine, carboxyl, thiol etc.

The term "$C_1$-$C_{10}$ heterosubstituted hydrocarbon" refers to a hydrocarbon chain having 1 to 10 C atoms in the backbone wherein at least one of the C atoms is substituted with an atom other than C such as nitrogen, oxygen, phosphorus, sulfur or a halogen atom. These substituents include but not limited to lower alkoxy such as methoxy, ethoxy, butoxy; ethers; acetals; ketals; esters; hetroaryl; heterocyclic; hydroxyl; protected hydroxyl; acyl; acyloxy; amino; amido; imine, disulfide, carbonate, carbamate, hydrozone, hydrazine.

In an embodiment of the invention, the linker (L) is GFLG. In an embodiment of the invention, the linker is Val-Cit. In an embodiment of the invention, the linker is Phe-Lys. In an embodiment of the invention, the linker is Val-Ala. In an embodiment of the invention, the linker is Ala-Leu-Ala-Leu.

In an embodiment of the invention, the linker is a $C_1$-$C_{10}$ hetero substituted hydrocarbon comprising at least one disulfide functional group. In an embodiment of the invention the linker is a $C_1$-$C_{10}$ hetero substituted hydrocarbon comprising at least one acetal functional group. In an embodiment of the invention the linker is a $C_1$-$C_{10}$ hetero substituted hydrocarbon comprising at least one ester functional group. In an embodiment of the invention the linker is a $C_1$-$C_{10}$ hetero substituted hydrocarbon comprising at least one imine functional group. In an embodiment of the invention the linker is a $C_1$-$C_{10}$ hetero substituted hydrocarbon comprising at least one amide functional group. In an embodiment of the invention the linker is a $C_1$-$C_{10}$ hetero substituted hydrocarbon comprising at least one carbonate functional group. In an embodiment of the invention the linker is a $C_1$-$C_{10}$ hetero substituted hydrocarbon comprising at least one carbamate functional group. In an embodiment of the invention the linker is a $C_1$-$C_{10}$ hetero substituted hydrocarbon comprising at least one hydrazone functional group.

In another embodiment of the invention the linker may comprise a $C_1$-$C_{10}$ substituted or hetero substituted hydrocarbon comprising two or more functional groups selected from the group comprising acetal, ester, imine, amide, disulfide, carbonate, carbamate, hydrazone.

In another embodiment of the invention the linker may be a combination of a $C_1$-$C_{10}$ substituted hydrocarbon comprising at least one functional group selected from the group comprising acetal, ester, imine, amide, disulfide, carbonate, carbamate, hydrazone and a peptide chain selected from the group comprising GFLG, Val-Cit or Phe-Lys or Val-Ala or Ala-Leu-Ala-Leu.

The term "therapeutic agent" refers to any compound that is suitable for use in treatment of a disease. The terms "therapeutic agent", "chemotherapy agent", "anticancer agent" and "antineoplastic agent" all refer to the compounds suitable for use in treatment of a disease and these terms can be used interchangeably. In one embodiment, the disease is cancer.

Additionally, a "therapeutic agent" also refers to any agent that is suitable for use in treating of a disease, for example cancer. Any therapeutic agent which can be directly or indirectly attached to the polymer-drug conjugate of the invention can be used. U.S. Pat. No. 6 6,342,221 also describe agents related to anticancer agents and this document is incorporated herein by reference. Anticancer agents can be classified as but are not limited to, chemotherapeutic agents, cytotoxins, antimetabolites, alkylating agents, protein kinase inhibitors, anthracyclines, antibiotics, antimitotic agents (e.g. antitubulin agents), corticosteroids, radiopharmaceuticals, and proteins (e.g. cytokines, enzymes, or interferons). Specific examples of anticancer agents are for example, docetaxel, gemcitabine, imatinib, 5-fluorouracil, 9-aminocamptothecin, amine-modified geldanamycin, doxorubicin, paclitaxel, procarbazine, hydroxyurea, meso e-chlorin, cisplatin and radionuclides (e.g 1-131, Y-90, In-111, and Tc-99m). There are many other anticancer agents known in the art and many continue to be developed, those agents are also included within the scope of this invention.

The therapeutic agent(s) can also be selected from a sub group comprising, but not limited to, nucleoside analogs, antifolates, other metabolites, topoisomerase I inhibitors, anthracyclines, podophyllotoxins, taxanes, vinca alkaloids, alkylating agents, platinum compounds, antihormones, radiopharmaceutics, monoclonal antibodies, tyrosine kinase inhibitors, mammalian target of rapamycin (mTOR) inhibitors, retinoids, immunomodulatory agents, histonedeacetylase inhibitors and other agents.

Nucleoside analogs can be selected from a group comprising, but not limited to, azacitidine, cladribine, clofarabine, cytarabine, decitabine, floxuridine, fludarabine, fluorouracil (5-FU), gemcitabine, mercaptopurine, nelarabine, pentostatin, tioguanine, trifluridine, tipiracil.

Antifolates can be selected from a group comprising, but not limited to, methotrexate, pemetrexed, pralatrexed, raltitrexed. Other metabolites can be selected from a group comprising, but not limited to, hydroxycarbamide. Topoisomerase I inhibitors can be selected from a group comprising, but not limited to, irinotecan and topotecan. Anthracyclines can be selected from a group comprising, but not limited to, daunorubicin, doxorubicin, epirubicin, idarubicin, mitoxantrone, valrubicin. Podophyllotoxins can be selected from a group comprising, but not limited to, etoposide and teniposide. Taxanes can be selected from a group comprising, but not limited to, cabazitaxel, docetaxel, paclitaxel. Vinca alkaloids can be selected from a group comprising, but not limited to, vinblastine, vincristine, vindesine, vinflunine, vinorelbine. Alkylating agents can be selected from a group comprising, but not limited to, bendamustine, chlorambucil, dacarbazine, melphalan, streptozotocin, trabectedin. Antihormone compounds can be selected from a group comprising, but not limited to, abiraterone, bicalutamide, cyproterone, degarelix, exemestane, fulvestrant, goserelin, histrelin, leuprolide, mifepristone, triptorelin. Tyrosine kinase inhibitors can be selected from a group comprising, but not limited to, afatinib, axitinib, bosutinib, cobimetinib, crizotinib, dasatinib, erlotinib, gefitinib, imatinib, lapatinib, nilotinib, osimertinib, pazopanib, ruxolitinib, sunitinib, vandetanib. Mammalian target of rapamycin (mTOR) inhibitors can be selected from a group comprising, but not limited to everolimus, temsirolimus. Retinoids can be selected from a group comprising, but not limited to, alitretinoin, bexarotene, isotretinoin, tamibarotene, tretinoin. Immunomodulatory agents can be selected from a group comprising, but not limited to, lenalidomide, pomalidomide, thalidomide. Histone deacetylase inhibitors can be selected from a group comprising, but not limited to, belinostat, panobinostat, valproate, vorinostat. Other agents can be selected from a group comprising, but not limited to, anagrelide, ceritinib, dabrafenib, idelalisib, ibrutinib, palbociclib, vemurafenib, bleomycin, bortezomib, dactinomycin, eribulin, estramustine, ixabepilone, mitomycin, procarbazine, alectinib, fluxymesterone, iobenguane, imiguimod, interferon, ixazomib, lanreotide, lentinan, octreotide, omacetaxine, tegafur, gimerazil, oteracil, uracil, combretastatin, chloroquine.

In a preferred embodiment of the invention the therapeutic agent(s) is selected from taxanes, antifolates, tyrosine kinase inhibitors, anthracyclines, nucleoside analogs or other agents. Most preferably the therapeutic agent(s) is selected from a group comprising docetaxel, pemetrexed, chloroquine, combretastatin, gemcitabine, doxorubicine, Fluorouracil (5-FU), 5'-Deoxy 5-Fluorocytidine (5'-DFCR), lapatinib and any of the therapeutic agents listed above. As such the therapeutic agents Herein the term “agent(s)” refer to at least one or more therapeutic agents.

In an embodiment of the invention the therapeutic agent is docetaxel. In an embodiment of the invention the therapeutic agent is pemetrexed. In an embodiment of the invention the therapeutic agent is chloroquine. In an embodiment of the invention the therapeutic agent is combretastatin. In an embodiment of the invention the therapeutic agent is gemcitabine. In an embodiment of the invention the therapeutic agent is doxorubicine. In an embodiment of the invention the therapeutic agent is 5-FU. In an embodiment of the invention the therapeutic agent is 5'-Deoxy 5-Fluorocytidine (5'-DFCR). In an embodiment of the invention the therapeutic agent is lapatinib.

In an embodiment of the invention the therapeutic agent is a combination of two or more therapeutic agents selected from the group comprising docetaxel, pemetrexed, chloroquine, combretastatin, gemcitabine, doxorubicine, 5-FU, 5'-Deoxy 5-Fluorocytidine (5'-DFCR) and lapatinib and any other agents listed above. As such therapeutic agent(s) that are a combination of two or more therapeutic agents can be selected from the main groups or specific members of the main groups listed above.

The therapeutic agent can be present in an amount in between 1% to 40% by weight of the polymer-drug conjugate, preferably in an amount between 2% to 35% by weight of the drug-polymer conjugate and most preferably in an amount between 3% to 30% by weight of the drug-polymer conjugate. The therapeutic agent can be present in an amount in the range of for example; 4% to 25% or 5% to 24% or 6% to 23% or 7% to 22% or 8% to 20% by weight of the drug-polymer conjugate.

The term “end group” refers to functionalities or constitutional units that are at the extremity of a polymer. The end groups shown as A and B can be identical to or different from one another.

A and B can optionally be a polymerization initiator or a fragment thereof. Particularly when an initiator is used in the polymerization reaction, the initiator fragment may stay as an end group to the polymer. The initiator used herein, may be any material suitable for initiating the polymerization reaction known in the art.

In one embodiment, A and/or B is selected from the group consisting of 4,4'-Azobis(4-cyanovaleric acid), 4,4'-Azobis (4-cyanovaleric acid), 1,1'-Azobis(cyclohexanecarbonitrile), 2,2'-Azobis(2-methylpropionamidine) dihydrochloride, 2,2'-Azobis(2-methylpropionitrile) (also known as AIBN), Ammonium persulfate, hydroxymethanesulfinic acid monosodium salt dihydrate, potassium persulfate, sodium persulfate, tert-Butyl hydroperoxide, tert-Butyl peracetate, Cumenehydroperoxide, 2,5-Di(tert-butylperoxy)-2, 5-dimethyl-3-hexyne, Dicumyl peroxide, 2,5-Bis(tert-butylperoxy)-2,5-dimethylhexane, 1,1-Bis(tert-butylperoxy)-3,3,5-trimethylcyclohexane, 1,1-Bis(tert-amylperoxy)cyclohexane, Benzoyl peroxide, 2-Butanone peroxide, tert-Butyl peroxide, Di-tert-amyl peroxide, Lauroyl peroxide, tert-Butyl peroxybenzoate, tert-Butylperoxy 2-ethylhexyl carbonate, tert-Butyl hydroperoxide, 2-Azidoethyl 2-bromoisobutyrate, Bis[2-(2-bromoisobutyryloxy) undecyl]disulfide, Bis[2-(2'-bromoisobutyryloxy)ethyl]disulfide, 2-Bromoisobutanoic acid N-hydroxysuccinimide ester, 2-Bromoisobutyric anhydride, α-Bromoisobutyryl bromide, 2-(2-Bromoisobutyryloxy)ethyl methacrylate, tert-Butyl α-bromoisobutyrate, 3-Butynyl 2-bromoisobutyrate, Dipentaerythritolhexakis(2-bromoisobutyrate), Dodecyl 2-bromoisobutyrate, Ethyl α-bromoisobutyrate, Ethylene bis(2-bromoisobutyrate), 2-Hydroxyethyl 2-bromoisobutyrate, 1-(DL-1,2-Isopropylideneglyceryl) 2-bromoisobutyrate, Methyl α-bromoisobutyrate, Octadecyl 2-bromoisobutyrate, Pentaerythritoltetrakis(2-bromoisobutyrate), 1-(Phthalimidomethyl) 2-bromoisobutyrate, Poly(ethylene glycol) bis(2-bromoisobutyrate), Propargyl 2-bromoisobutyrate, 1,1,1-Tris(2-bromoisobutyryloxymethyl)ethane, 10-Undecenyl 2-bromoisobutyrate, N-tert-Butyl-O-[1-[4-(chloromethyl)phenyl]ethyl]-N-(2-methyl-1-phenylpropyl) hydroxylamine, N-tert-Butyl-N-(2-methyl-1-phenylpropyl)-O-(1-phenylethyl)hydroxylamine, TEMPO, TEMPO methacrylate, 2,2,5-Trimethyl-4-phenyl-3-azahexane-3-nitroxide, 3,5-Bis(2-dodecylthiocarbonothioylthio-1-oxopropoxy)benzoic acid, 3-Butenyl 2-(dodecylthiocarbonothioylthio)-2-methylpropionate, 4-Cyano-4-[(dodecylsulfanylthiocarbonyl)sulfanyl]pentanoic acid, 4-Cyano-4-[(dodecylsulfanylthiocarbonyl)sulfanyl]pentanol, Cyanomethyl dodecyl, Cyanomethyl [3-(trimethoxysilyl)propyl]trithiocarbonate, 2-Cyano-2-propyl dodecyl trithiocarbonate, S,S-Dibenzyl trithiocarbonate, 2-(Dodecylthiocarbonothioylthio)-2-methylpropionic acid, 2-(Dodecylthiocarbonothioylthio)-2-methylpropionic acid, 3-azido-1-propanol ester, 2-(Dodecylthiocarbonothioylthio)-2-methylpropionic acid N-hydroxysuccinimide ester, 2-(Dodecylthiocarbonothioylthio)-2-methylpropionic acid pentafluorophenyl ester, 2-(Dodecylthiocarbonothioylthio) propionic acid, Methyl 2-(dodecylthiocarbonothioylthio)-2-methylpropionate, Pentaerythritol tetrakis[2-(dodecylthiocarbonothioylthio)-2-methylpropionate], Phthalimidomethyl butyl trithiocarbonate, 1,1,1-Tris[(dodecylthiocarbonothioylthio)-2-methylpropionate]ethane, benzyl benzodithioate, Cyanomethyl benzodithioate, 4-Cyano-4-(phenylcarbonothioylthio)pentanoic acid, 4-Cyano-4-(phenylcarbonothioylthio)pentanoic acid N-succinimidyl ester, 2-Cyano-2-propyl benzodithioate, 2-Cyano-2-propyl 4-cyanobenzodithioate, Ethyl 2-(4-methoxyphenylcarbonothioylthio)acetate, Ethyl 2-methyl-2-(phenylthiocarbonylthio)propionate, Ethyl 2-(phenylcarbonothioylthio)-2-phenylacetate, Ethyl 2-(phenylcarbonothioylthio)propionate, 1-(Methoxycarbonyl) ethyl benzodithioate, 2-(4-Methoxyphenylcarbonothioylthio)ethanoic acid, 2-Nitro-5-(2-propynyloxy)benzyl, 4-cyano-4-(phenylcarbonothioylthio)pentanoate, 2-(Phenylcarbonothioylthio)propanoic acid, 2-Phenyl-2-propyl benzodithioate, Cyanomethyl methyl(4-pyridyl)carbamodithioate, Cyanopropan-2-yl N-methyl-N-(pyridin-4-yl) carbamodithioate, Methyl 2-[methyl(4-pyridinyl) carbamothioylthio]propionate, 1-Succinimidyl-4-cyano-4-[N-methyl-N-(4-pyridyl)carbamothioylthio]pentanoate or any fragment of the initiators listed herein.

The term “fragment” as used herein refers to compounds that form due to breaking of one or more of the covalent bonds forming the initiator molecule.

A and/or B is optionally null.

In an embodiment of the invention A is null and B is a polymerization initiator or a fragment of a polymerization initiator. In another embodiment B is null and A is a polymerization initiator or a fragment of a polymerization initiator. In another embodiment A and B are both fragments of a polymerization initiator however they are structurally different from one another. In other words, A and B are different fragments of the same initiator. In another embodiment A and B are both fragments of a polymerization initiator and they have the same chemical structure.

In some of the preferred embodiments, the polymer drug conjugate of invention comprise one or more of the following;

GFLG as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

Val-Cit as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

Phe-Lys as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

Val-Ala as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

Ala-Leu-Ala-Leu as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one disulfide functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one acetal functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one ester functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one imine functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one amide functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one carbonate functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one carbamate functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ hetero substituted hydrocarbon comprising at least one hydrazone functional group as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A $C_1$-$C_{10}$ substituted or hetero substituted hydrocarbon comprising two or more functional groups selected from the group comprising acetal, ester, imine, amide, disulfide, carbonate, carbamate, hydrazone as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

A combination of a $C_1$-$C_{10}$ substituted hydrocarbon comprising at least one functional group selected from the group comprising acetal, ester, imine, amide, disulfide, carbonate, carbamate, hydrazone and a peptide chain selected from the group comprising GFLG, Val-Cit, Val-Ala, Ala-Leu-Ala-Leu or Phe-Lys as the linker (L) and a therapeutic agent selected from the group docetaxel, pemetrexed, chloroquine, combretastatin, gemcitabine, doxorubicine, 5-FU, 5'-Deoxy 5-Fluorocytidine (5'-DFCR) and lapatinib.

The measurement of the amount of drug in the polymer conjugate of the invention is made by using conventional techniques well-known in the art, for example by calculation of the drug ratio from an $^1$H-NMR of the polymer-drug conjugate.

In another embodiment the polymer-drug of the invention has an average molecular weight in between 20 kDa to 300 kDa. In a preferred embodiment the polymer-drug conjugate of the invention has an average molecular weight in between, 30 Da to 270 kDa and in a most preferred embodiment the polymer-drug conjugate of the invention has an average molecular weight in between 40 kDa to 250 kDa.

Molecular weight of the polymer-drug conjugate of the invention is determined by using conventional techniques known in the art for example by using gel permeation chromatography (GPC).

Another embodiment of the invention is a method (Method I) for preparation of the polymer-drug conjugate of the invention (formula I) which comprises polymerization of PEG (meth)acrylate monomer (Formula II)

Formula II

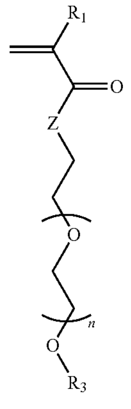

and at least one type of (meth)acrylate-L-D monomer (Formula IIIa)

Formula IIIa

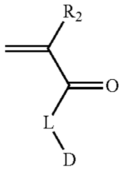

wherein $R_1$ and $R_2$ are independently selected from H or —$CH_3$ $R_3$ is selected from —H or $CH_3$ L is a cleavable linker D is at least one therapeutic agent and n is a natural number between 1-200

In another aspect, a method (Method II) for preparation of the polymer-drug conjugate of the invention (formula I) comprises (i) polymerization of PEG (meth)acrylate monomer (Formula II)

Formula II

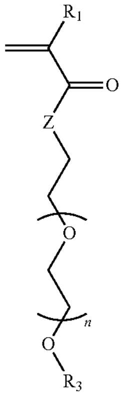

and (meth)acrylate-L monomer (Formula IIIb)

Formula IIIb

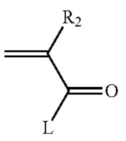

wherein $R_1$ and $R_2$ are independently selected from H or —$CH_3$

R3 is selected from —H or —$CH_3$

L is a cleavable linker and n is a natural number between 1-200

To give a copolymer as shown in formula IV

Formula IV

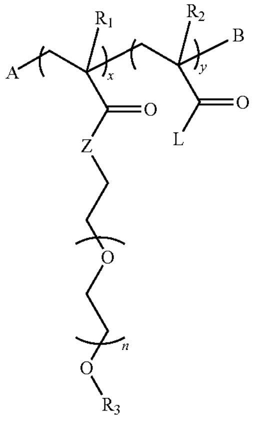

wherein x is a natural number between 1-100 and y is a natural number between 1-100

Z is selected from —O or —NH

A is an end group that is optionally a polymerization initiator or a fragment thereof or A may be null B is an end group that is optionally a polymerization initiator or a fragment thereof or B may be null and then (ii) reacting formula IV with at least one type of therapeutic agent (D) to give polymer conjugate shown in formula I.

In another aspect, a method (method III) for preparation of the polymer-drug conjugate of the invention (formula I) comprises (i) polymerization of PEG (meth)acrylate monomer shown with Formula II Formula II

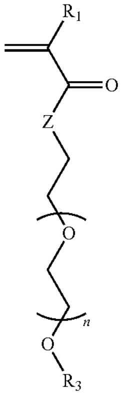

and (meth)acrylate monomer shown with Formula IIIc

Formula IIIc

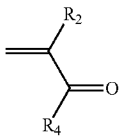

wherein n is a natural number between 1-200 and $R_1$ and $R_2$ are independently selected from H or —$CH_3$ $R_3$ is selected from —H or —$CH_3$ $R_4$ is selected from carbonyl activating groups such as perfluorophenoxy, maleimide, carbonate, thiazolidone-2-thione, N-oxybenzotriazole, imidazolyl, o/p-nitrophenol, pentachloro-phenol, N-hydroxysuccinimide, acetates, formates, 2,3,5-trichlorophenol, 8-hydroxyquinoline, —$OCH_3$, —$OCH_2CH_3$, Cl, F, Br, H, —SH, —$NH_2$, —$NHR_5$ or —$OR_5$ wherein $R_5$ is $C_1$-$C_{10}$ saturated or unsaturated hydrocarbon to give a copolymer as shown in formula V Formula V

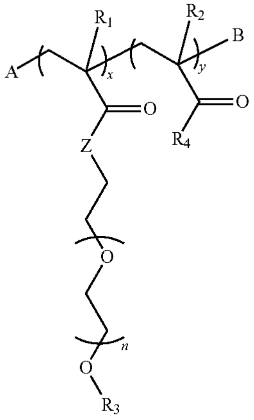

wherein x is a natural number between 1-100 and y is a natural number between 1-100, Z is selected from —O or —NH A is an end group that is optionally a polymerization initiator or a fragment thereof or A may be null B is an end group that is optionally a polymerization initiator or a fragment thereof or B may be null and then (ii) reacting formula V with at least one type of therapeutic agent attached to a linker (L-D) to give polymer conjugate of formula I.

Herein the term "carbonyl activating group" refers to leaving group of a carboxyl derivative that is easily replaced by an incoming nucleophile.

In another aspect, a method (method IV) for preparation of the polymer-drug conjugate of the invention (formula I) comprises (i) polymerization of PEG (meth)acrylate monomer (Formula II)

Formula II

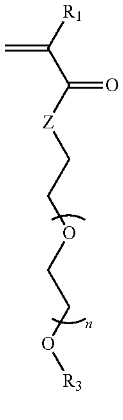

and (meth)acrylate monomer (Formula IIIc)

Formula IIIc

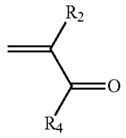

wherein n is a natural number between 1-200 and $R_1$ and $R_2$ are independently selected from H or —$CH_3$ $R_3$ is selected from —H or —$CH_3$ $R_4$ is selected from carbonyl activating groups such as perfluorophenoxy, maleimide, carbonate, thiazolidone-2-thione, N-oxybenzotriazole, imidazolyl, o/p-nitrophenoxy, pentachloro-phenoxy, N-hydroxysuccinimide, acetates, formates, 2,3,5-trichlorophenol, 8-hydroxyquinoline, —OH, —$OCH_3$, —$OCH_2CH_3$, Cl, F, Br, H, —SH, —$NH_2$, —$NHR_5$ or —$OR_5$ wherein $R_5$ is $C_1$-$C_{10}$ saturated or unsaturated hydrocarbon to give a copolymer as shown in formula V Formula V

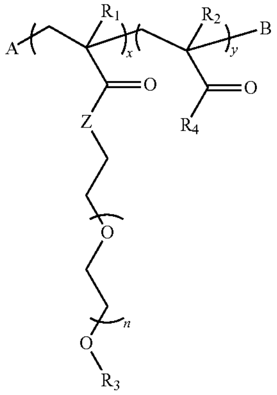

wherein x is a natural number between 1-100 and y is a natural number between 1-100, Z is selected from —O or —NH A is an end group that is optionally a polymerization initiator or a fragment thereof or A may be null B is an end groups that is optionally a polymerization initiator or a fragment thereof or B may be null and (ii) reacting formula V with a linker (L) to give a copolymer as shown in formula IV Formula IV

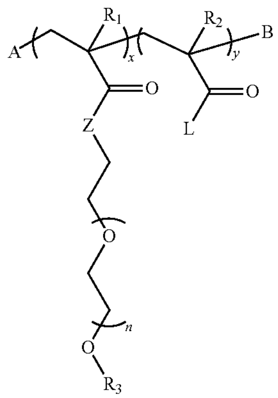

wherein n, x, y, $R_1$, $R_2$ and $R_3$ are as described above and (iii) reacting formula IV with at least one type of therapeutic agent (D) to give polymer conjugate shown in formula I.

Within this document the terms "at least one therapeutic agent" and "at least one type of therapeutic agent" are used interchangeably and refer to use of structurally different therapeutic agents or in other words refer to attachment of one or more such as two, three, four etc. different therapeutic agents onto the polymers according to present invention, as such the terms does not refer to quantitative amount used in the polymer structure. Similarly, the term "at least one type of (meth)acrylate-L-D monomer" refers to monomer structures having one or more such as two, three or four etc. different therapeutic agents as molecule D.

In another aspect, the invention relates to polymer-drug conjugate of formula I prepared by any one of the methods I, II, III or IV. Polymer-drug conjugate of formula I prepared by methods I, II, III or IV has a random copolymer structure which has advantageous technical effects.

In one embodiment, PEG (meth)acrylate (Formula II) is preferably selected from a group comprising; polyethylene glycol methyl ether methacrylate (CAS No: 26915-72-0), polyethylene glycol methacrylate (CAS No: 25736-86-1), polyethylene glycol methyl ether acrylate (CAS No: 32171-39-4), and poly ethylene glycol acrylate (CAS No: 9051-31-4), see table 1 for structures of the compounds. In a preferred embodiment of the invention, polyethylene glycol methyl ether methacrylate, wherein $R_1$ and $R_3$ are both-$CH_3$, is used.

In an embodiment of the invention PEG (meth)acrylate (Formula II) has an average molecular weight in between 200-2000 g/mol is used. In a preferred embodiment PEG (meth)acrylate (Formula II) has an average molecular weight in between 250-1500 g/mol and in a most preferred embodiment PEG (meth)acrylate (Formula II) has an average molecular weight in between 300-1100 g/mol. PEG (meth)acrylate (Formula II) of the invention can have an average molecular weight of for example 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 g/mol.

The cleavable linker according to present invention can be obtained from commercial sources or may be prepared according to known methods provided in literature.

In another aspect, present invention relates to a copolymer of formula IV for use in synthesis of polymer drug conjugate of formula I Formula IV

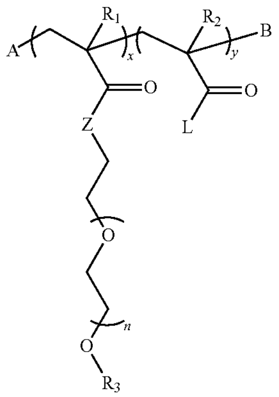

wherein;

x is a natural number between 1-100, y is a natural number between 1-100, $R_1$ and $R_2$ are independently selected from H or —$CH_3$, $R_3$ is selected from —H or —$CH_3$ or —$CH_2CH_3$, n is a natural number between 1-200 and, L is a cleavable linker Z is selected from —O or —NH A is an end group that is optionally a polymerization initiator or a fragment thereof or A may be null B is an end group that is optionally a polymerization initiator or a fragment thereof or B may be null.

In another aspect, present invention relates to a copolymer of formula V for use in synthesis of polymer drug conjugate of formula I Formula V

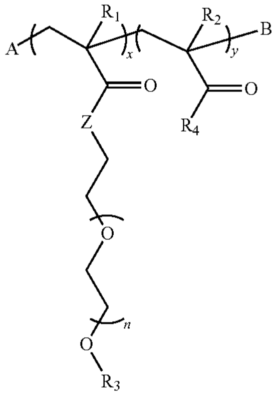

wherein;

x is a natural number between 1-100, y is a natural number between 1-100, $R_1$ and $R_2$ are independently selected from H or —$CH_3$;

$R_3$ is selected from —H or —$CH_3$ or —$CH_2CH_3$;

Z is selected from —O or —NH $R_4$ is selected from carbonyl activating groups such as perfluorophenoxy, maleimide, carbonate, thiazolidone-2-thione, N-oxybenzotriazole, imidazolyl, o/p-nitrophenoxy, pentachloro-phenoxy, N-hydroxysuccinimide, acetates, formates, 2,3,5-trichlorophenol, 8-hydroxyquinoline and —OH, —$OCH_3$, —$OCH_2CH_3$, Cl, F, Br, H, —SH, —$NH_2$, —$NHR_5$ or —$OR_5$, $R_5$ is $C_1$-$C_{10}$ saturated or unsaturated hydrocarbon n is a natural number between 1-200

A is an end group that is optionally a polymerization initiator or a fragment thereof or A may be null B is an end group that is optionally a polymerization initiator or a fragment thereof or B may be null.

As disclosed above, methods for preparing the polymer drug conjugate of formula I (Method I, II, III and IV) comprise at least one polymerization step, wherein monomers formula II and monomers of formula IIIa or IIIb or IIIc are polymerized. In an embodiment of the invention, these polymerization steps further comprise an initiator and/or a solvent.

The polymer-drug conjugate of the invention can be prepared by any of the known polymerization methods. Any suitable initiators and/or catalysts known in the art can be used for the preparation of the polymer-drug conjugate of the present invention. Where a polymerization initiator is used, the initiator or a fragment thereof may be present in the resulting polymer-drug conjugate.

The polymer backbone of the polymer-drug conjugate of the invention can be obtained by for example bulk polymerization, solution polymerization and/or suspension polymerization techniques known in the art.

The polymerization technique used for the preparation of the polymer-drug conjugate of the present invention may propagate through free-radical polymerization or controlled/living free radical polymerization. Herein the term "controlled/living free radical polymerization" refers to atom transfer radical polymerization (ATRP), Reversible addition fragmentation chain transfer (RAFT) polymerization, iodine transfer polymerization (ITP), selenium centered radical mediated polymerization, telluride mediated polymerization (TERP), nitroxide mediated polymerization (NMP). In a preferred embodiment of the invention RAFT polymerization is used to prepare the polymer-drug conjugates of the invention.

A polymerization initiator as used herein refers to a chemical compound that reacts with a monomer to form an intermediate compound capable of linking successively with a large number of other monomers into a polymeric compound.

In an embodiment of the invention a polymerization initiator selected from the group 4,4'-Azobis(4-cyanovaleric acid), 4,4'-Azobis(4-cyanovaleric acid), 1,1'-Azobis(cyclohexanecarbonitrile), 2,2'-Azobis(2-methylpropionamidine) dihydrochloride, 2,2'-Azobis(2-methylpropionitrile) (also known as AIBN), Ammonium persulfate, hydroxymethanesulfinic acid monosodium salt dihydrate, potassium persulfate, sodium persulfate, tert-Butyl hydroperoxide, tert-Butyl peracetate, Cumenehydroperoxide, 2,5-Di(tert-butylperoxy)-2,5-dimethyl-3-hexyne, Dicumyl peroxide, 2,5-Bis (tert-butylperoxy)-2,5-dimethylhexane, 1,1-Bis(tert-butylperoxy)-3,3,5-trimethylcyclohexane, 1,1-Bis(tert-amylperoxy)cyclohexane, Benzoyl peroxide, 2-Butanone peroxide, tert-Butyl peroxide, Di-tert-amyl peroxide, Lauroyl peroxide, tert-Butyl peroxybenzoate, tert-Butylperoxy 2-ethylhexyl carbonate, tert-Butyl hydroperoxide, 2-Azidoethyl 2-bromoisobutyrate, Bis[2-(2-bromoisobutyryloxy) undecyl]disulfide, Bis[2-(2'-bromoisobutyryloxy)ethyl]disulfide, 2-Bromoisobutanoic acid N-hydroxysuccinimide ester, 2-Bromoisobutyric anhydride, α-Bromoisobutyryl bromide, 2-(2-Bromoisobutyryloxy)ethyl methacrylate, tert-Butyl α-bromoisobutyrate, 3-Butynyl 2-bromoisobutyrate, Dipentaerythritolhexakis(2-bromoisobutyrate), Dodecyl 2-bromoisobutyrate, Ethyl α-bromoisobutyrate, Ethylene bis(2-bromoisobutyrate), 2-Hydroxyethyl 2-bromoisobutyrate, 1-(DL-1,2-Isopropylideneglyceryl) 2-bromoisobutyrate, Methyl α-bromoisobutyrate, Octadecyl 2-bromoisobutyrate, Pentaerythritoltetrakis(2-bromoisobutyrate), 1-(Phthalimidomethyl) 2-bromoisobutyrate, Poly(ethylene glycol) bis(2-bromoisobutyrate), Propargyl 2-bromoisobutyrate, 1,1,1-Tris(2-bromoisobutyryloxymethyl)ethane, 10-Undecenyl 2-bromoisobutyrate, N-tert-Butyl-O-[1-[4-(chloromethyl)phenyl]ethyl]-N-(2-methyl-1-phenylpropyl) hydroxylamine, N-tert-Butyl-N-(2-methyl-1-phenylpropyl)-O-(1-phenylethyl)hydroxylamine, TEMPO, TEMPO methacrylate, 2,2,5-Trimethyl-4-phenyl-3-azahexane-3-nitroxide, 3,5-Bis(2-dodecylthiocarbonothioylthio-1-oxopropoxy)benzoic acid, 3-Butenyl 2-(dodecylthiocarbonothioylthio)-2-methylpropionate, 4-Cyano-4-[(dodecylsulfanylthiocarbonyl)sulfanyl]pentanoic acid, 4-Cyano-4-[(dodecylsulfanylthiocarbonyl)sulfanyl]pentanol, Cyanomethyl dodecyl, Cyanomethyl [3-(trimethoxysilyl)propyl]trithiocarbonate, 2-Cyano-2-propyl dodecyl trithiocarbonate, S,S-Dibenzyl trithiocarbonate, 2-(Dodecylthiocarbonothioylthio)-2-methylpropionic acid, 2-(Dodecylthiocarbonothioylthio)-2-methylpropionic acid, 3-azido-1-propanol ester, 2-(Dodecylthiocarbonothioylthio)-2-methylpropionic acid N-hydroxysuccinimide ester, 2-(Dodecylthiocarbonothioylthio)-2-methylpropionic acid pentafluorophenyl ester, 2-(Dodecylthiocarbonothioylthio) propionic acid, Methyl 2-(dodecylthiocarbonothioylthio)-2-methylpropionate, Pentaerythritol tetrakis[2-(dodecylthiocarbonothioylthio)-2-methylpropionate], Phthalimidomethyl butyl trithiocarbonate, 1,1,1-Tris[(dodecylthiocarbonothioylthio)-2-methylpropionate]ethane, benzyl benzodithioate, Cyanomethyl benzodithioate, 4-Cyano-4-(phenylcarbonothioylthio)pentanoic acid, 4-Cyano-4-(phenylcarbonothioylthio)pentanoic acid N-succinimidyl ester, 2-Cyano-2-propyl benzodithioate, 2-Cyano-2-propyl 4-cyanobenzodithioate, Ethyl 2-(4-methoxyphenylcarbonothioylthio)acetate, Ethyl 2-methyl-2-(phenylthiocarbonylthio)propionate, Ethyl 2-(phenylcarbonothioylthio)-2-phenylacetate, Ethyl 2-(phenylcarbonothioylthio)propionate, 1-(Methoxycarbonyl) ethyl benzodithioate, 2-(4-Methoxyphenylcarbonothioylthio)ethanoic acid, 2-Nitro-5-(2-propynyloxy)benzyl, 4-cyano-4-(phenylcarbonothioylthio)pentanoate, 2-(Phenylcarbonothioylthio)propanoic acid, 2-Phenyl-2-propyl benzodithioate, Cyanomethyl methyl(4-pyridyl)carbamodithioate, Cyanopropan-2-yl N-methyl-N-(pyridin-4-yl) carbamodithioate, Methyl 2-[methyl(4-pyridinyl) carbamothioylthio]propionate, 1-Succinimidyl-4-cyano-4-[N-methyl-N-(4-pyridyl)carbamothioylthio]pentanoate or a combination thereof. In an embodiment of the invention AIBN is used as the initiator. Thus, in an embodiment of the invention methods I, II, III and/or IV used to prepare the polymer-conjugate of formula I comprises use of AIBN as initiator in the polymerization reactions.

In an embodiment of the invention the polymer-drug conjugate of the invention can further comprise targeting groups. Herein the term "targeting group" refers to tumor specific ligands that bind specifically to the cell, preferably the tumor cell that has a complimentary receptor.

The term "targeting group" means a molecule which serves to deliver the polymer-drug conjugate of the invention to a specific site for the desired activity, i.e. it provides localization of the compound. The localization is mediated by specific recognition of molecular determinants, molecular size of the targeting agent or conjugate, ionic interactions, hydrophobic interactions, and the like. Other mechanisms of targeting an agent to a particular tissue or region are known to those of skill in the art. Targeting ligands include, for example, molecules that bind to molecules on a targeted cell surface. Exemplary targeting ligands include antibodies, antibody fragments, small organic molecules, peptides, peptoids, proteins, polypeptides, oligosaccharides, transferrin, HS-glycoprotein, coagulation factors, serum proteins, beta-glycoprotein, G-CSF, GM-CSF, M-CSF, EPO, and the like. In exemplary embodiments of the present invention, the targeting system includes covalently attaching a targeting ligand such as RGDfK, EPPTl peptide, bisphosphonic acid or folate to the carrier molecule or linker.

In certain embodiments, the present invention is characterized by polymer-drug conjugates with or without a targeting ligand. In some embodiments the targeting ligand can be RGDfK, EPPT1, bisphosphonic acid or folate.

Another embodiment of the present invention provides a method for delivering a therapeutic agent, comprising administering to a subject an effective amount of polymer-drug conjugate shown with formula I.

Another embodiment of the invention is the polymer-drug conjugate of the invention for use in treatment of a variety of disorders that require the delivery of anticancer or similar agents.

In a preferred embodiment, the invention is related to a polymer-drug conjugate shown with formula I for use as a medicament for treatment of cancer.

As used herein, "treat" or "treating" means to inhibit, reduce, modulate, ameliorate, or block at least one symptom that characterizes a pathologic condition, in a subject threatened by, or afflicted with, the condition. A non-limiting list of different types of cancers is as follows: carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, metastatic cancers, or cancers in general. Specific examples of of cancers that the disclosed compositions can be used to treat include B cell lymphoma, T cell lymphoma, mycosis fungoides, Hodgkin's Disease, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Polymer-drug conjugates of the invention may also be used for the treatment of precancer conditions such as cervical and anal dysplasias, other dysplasias, severe dysplasias, hyperplasias, atypical hyperplasias, and neoplasias.

The terms "cancer" and "cancerous" as used herein refers to malignant tumors or describe the physiological condition characterized by unregulated cell growth.

As discussed herein, polymer-drug conjugates of the present invention find use in the treatment and/or prophylaxis of cancer. For such use the polymer-drug conjugate of the present invention will generally be administered in the form of a pharmaceutical composition.

Thus, according to the invention there is provided a pharmaceutical composition comprising a polymer-drug conjugate according to formula I and at least one pharmaceutically acceptable diluent, excipient and/or carrier. The term "treatment" includes either therapeutic or prophylactic therapy.

The composition comprising the polymer-drug conjugate of the invention may be in any suitable form depending upon the desired method of administering it to a patient. The composition comprising polymer drug conjugates of the invention can be formulated to be administered orally, e.g. in the form of liquid dispersions or aqueous or oily suspensions or they can formulated for parenteral administration, for example for subcutaneous, intravenous, intramuscular, intrasternal, intraperitoneal, intradermal, transdermal or other infusion techniques. The composition comprising the polymer drug conjugates of the invention can also be formulated for administration by inhalation in form of an aerosol or solution for administration with and inhaler or nebulizer. The polymer-drug conjugates of the invention are preferably administered to a subject transdermally, subcutaneously, intranasally, intravenously, intramuscularly, intratumorally or via inhalation. The most suitable route for administration in any given case will depend on the particular therapeutic agent present in the polymer-drug conjugate of the present invention, the subject, and the nature and severity of the disease and the physical condition of the subject.

The polymer-drug conjugates of the invention may be administered in combination, e.g. simultaneously, sequentially or separately, with one or more other therapeutically active compounds, which may be an anti-cancer agent or it is an immunomodulatory, antiviral, antiinfective, antimicrobial, antiinfective or anesthetic agent or combinations thereof.

Said second therapeutic agent can be selected from the therapeutic agents listed above on the condition that it is different from the one present in the polymer-drug conjugate of the invention.

Comprising in the context of the present specification is intended to meaning including.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The invention will now be described with reference to the following examples, which are merely illustrative and should not in any way be construed as limiting the scope of the present invention.

EXAMPLES

Example 1: Preparation of Glycine-Phenylalanine-Leucine-Glycine (GFLG) Cleavable Linker Having a Methacrylate Functional Group The GFGL-MA linker was prepared according to the literature method described in K. Ulbrich et al., *Journal of Controlled Release,* 64, 2000, 63-79.

Example 2: Preparation of Docetaxel-GFGL-Methacrylate (MA) Monomer

Docetaxel (DTX) was coupled with the GFGL-MA linker according to the literature method described in Ghandehari et al., *Mol. Pharm.,* 2011, 8(4), 1090-1099 to give DTX-GFLG-MA.

Docetaxel, (0.335 g, 4.1 mmol), 4-(dimethylamino-) pyridine (DMAP, 0.049 g, 4.0 mmol) and MA-GFLG-OH (0.188 g, 4.0 mmol) were dried under vacuum. The reaction mixture was dissolved under nitrogen in anhydrous N, N-dimethylformamide (DMF, 5 mL), cooled with an ice bath (salt/ice) at <0° C. and diisopropylcarbodiimide (DIPC, 76 μL, 4.89 mmol) was added dropwise.

The reaction mixture was subsequently stirred for an hour before the ice bath was removed and the mixture was allowed to warm up to room temperature, stirred overnight and progress was monitored by thin layer chromatography (TLC, eluent dichloromethane (DCM):methanol (MeOH) (95:5)) for the disappearance of the starting material and the formation of MA-GFLG-Docetaxel. DMF was removed under vacuum using rotary evaporator. The product was purified by silica gel chromatography.

Example 3: Preparation of Polymer-Drug Conjugate Comprising Docetaxel and PEG in the Side Chains Polyethylene glycol methyl ether methacrylate (PEGMEMA) (Mn: 300) and DTX-GFGL-MA was polymerized in presence of AIBN as initiator and DMF as solvent to yield PEGMEMA-DTX.

Scheme 1: Schematic representation of copolymerization of PEGMEMA and DTX-GFLG-MA monomers.

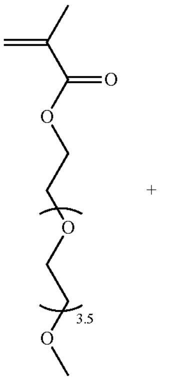

PEGMEMA

+

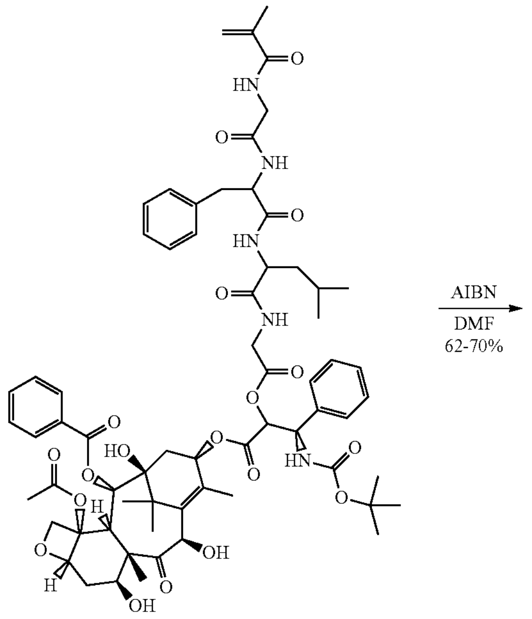

DTX-Monomer

-continued

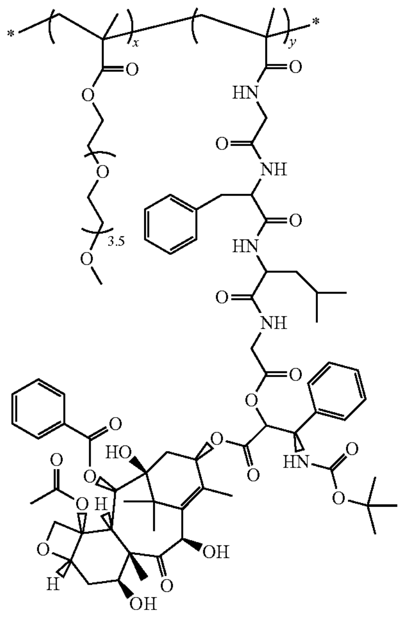

PEGMEMA-DTX Conjugate

In the above figure (*) represents the AIBN fragments as the end groups of the polymer-drug conjugate.

By varying the ratio of the PEGMEMA it is possible to obtain PEGMEMA-DTX conjugates having different molecular weights.

In order to demonstrate that the invention is applicable over various molecular weights of PEGMEMA-DTX conjugates, the inventors prepared 50 kDa and 85 kDa PEGMEMA-DTX polymer-drug conjugates and subjected them to pharmacokinetic testing.

Example 4: Results of Pharmacokinetic Study

PEGMEMA-DTX conjugates having 50 kDa and 85 kDa molecular weight were subjected to pharmacokinetic testing and its pharmacokinetic profile was compared with that of free DTX.

Pharmacokinetic parameters for total DTX were calculated using the plasma total DTX concentration values of polymer drug conjugates and free DTX. Half-life, volume of distribution (VDβ), clearance (CL), and total area under the curve (AUC total) were calculated.

For the sake of comparison with the known prior art, the applicants have prepared N-(2-hydroxypropyl)methacrylamide (HPMA)-GFLG-DTX polymers having molecular weight of 52 kDa and 85 kDa according to the known prior art methods disclosed in Ghandehari et al., *Mol. Pharm.*, 2011, 8(4), 1090-1099. In order to provide similarity the HPMA-GFLG-DTX polymer was prepared without RGDfK targeting group.

The results of pharmacokinetic tests are shown in Table 1.

TABLE 1

Pharmacokinetic parameters of PEGMEMA-GFLG-DTX conjugates, HPMA-GFLG-DTX conjugates and free DTX

| | Half Life (β)(hour) | $VD_\beta$ (mL) | CL (mL/hr) | AUC total (ug/mL.hr) |
|---|---|---|---|---|
| Free DTX | 3.12 ± 0.88 | 664.1 ± 258.1 | 140.4 ± 42.1 | 10 ± 3 |
| HPMA 52 kDa-DTX | 11.99 ± 0.37 | 102.5 ± 13.8 | 5.9 ± 0.7 | 241 ± 32 |
| HPMA 85 kDa-DTX | 16.24 ± 4.40 | 60.2 ± 11.1 | 2.6 ± 0.2 | 525 ± 57 |
| PEGMEMA 50 kDa-DTX | 14.62 ± 0.54 | 20.2 ± 1.9 | 1.0 ± 0.1 | 1357 ± 109 |
| PEGMEMA 85 kDa-DTX | 12.10 ± 0.35 | 10.0 ± 0.2 | 0.6 ± 0.0 | 2370 ± 106 |

When table 1 is taken into account, it is seen that both PEGMEMA-DTX conjugates have superior pharmacokinetic properties compared to the free therapeutic agent and HPMA-DTX conjugate. This result is indicative of the fact that the polymer-drug conjugate of the present invention provides a superior polymer-drug conjugate having longer half-life, lower clearance and larger AUC with respect to free DTX and DTX bound to HPMA polymer.

Example 5: Cytotoxicity Results of PEGMEMA-DTX Conjugates and Free DTX for BxPC3 Cells Human pancreas adenocarcinoma (BxPC3) cells were treated with conjugates and free DTX for 72 hours in DMEM medium. CCK-8 assay was performed to measure cell viability. PEGMEMA-DTX conjugates showed less cytotoxicity compared to free DTX conjugates which are desirable. The $EC_{50}$ values of the polymer drug conjugates and free DTX are shown in table 2.

TABLE 2

EC50 values of Free DTX and PEGMEMA-DTX conjugates

| | $EC_{50}$ Values [M] |
|---|---|
| Free DTX | $<1.0 \times 10^{-13}$ |
| PEGMEMA 50 kDa-DTX | $9.1 \times 10^{-11}$ |
| PEGMEMA 85 kDa-DTX | $3.0 \times 10^{-9}$ |

Example 6: Blood Toxicity of PEGMEMA-DTX and Free DTX

Blood samples (200 μL) were collected just before and after 24 hours of the injection. Whole blood counter was used to measure the hemogram values of the samples. The relative change after 24 hours of the injection compared to before injection values were presented in FIG. 1. White Blood Cell (WBC) Red Blood Cell (RBC) and Haemoglobin (HGB) and Haematocrit (HCT) values were evaluated. Low molecular weight conjugates had lower toxicity compared to high molecular weight ones on WBC. All conjugates showed less toxicity on RBC compared with free DTX. These results were also validated with HGB and HCT.

All in all, the results of the pharmacokinetic testing and cell and blood toxicity testing show that polymer-drug conjugates of the invention have better and unexpected properties with respect to known prior art and thus the present invention surpass the current state of the art.

EXPLANATION OF DRAWINGS

FIG. 1 is a graph showing percent hemogram values of PEGMEMA-DTX conjugates and free DTX.

The invention claimed is:

1. A polymer-drug conjugate having a formula I

Formula I

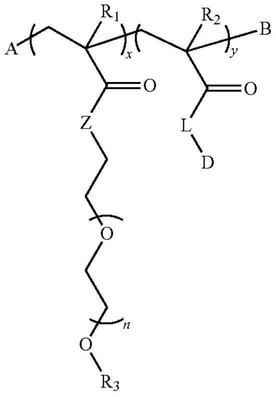

wherein $R_1$ and $R_2$ are independently selected from —$CH_3$; $R_3$ is selected from —H or —$CH_3$;

n is a natural number between 1-200;

L is a cleavable linker;

D is at least one anticancer agent selected from the group consisting of docetaxel, gemcitabine, or combretastatin;

Z is selected from —O;

A is an end group that is optionally a polymerization initiator or a fragment thereof;

B is an end group that is optionally a polymerization initiator or a fragment thereof; and Formula I is a random copolymer, x and y are each independently a natural number such that the polymer-drug conjugate has a molecular weight between 20 kDa to 300 kDa, wherein the linker is selected from the group consisting of: Gly-Phe-Leu-Gly (SEQ ID NO: 1), and a $C_1$-$C_{10}$ substituted or hetero substituted hydrocarbon comprising two or more functional groups selected from the group consisting of disulfide, carbonate, carbamate, or a combination thereof.

2. The polymer drug conjugate of claim 1 wherein the linker is Gly-Phe-Leu-Gly (SEQ ID NO: 1).

3. The polymer drug conjugate of claim 1 having the formula VI:

Formula VI

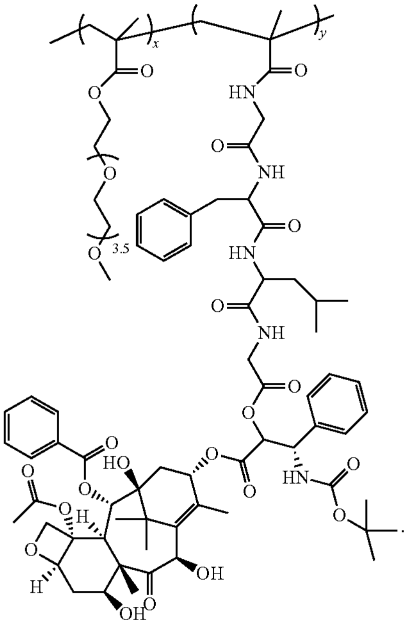

4. The polymer drug conjugate of claim 1, wherein one or both of the end groups is a polymerization initiator or a fragment thereof.

5. The polymer-drug conjugate of claim 1, wherein the anti-cancer agent is gemcitabine and the linker comprises disulfide.

6. The polymer-drug conjugate of claim 1, wherein the anti-cancer agent is gemcitabine and the linker comprises carbamate.

7. The polymer-drug conjugate of claim 1, wherein the anti-cancer agent is docetaxel and the linker comprises GFLG.

8. The polymer-drug conjugate according to claim 1, wherein the polymer conjugate comprises a first anti-cancer agent and a second-cancer agent.

9. The polymer-drug conjugate of claim 8, wherein the first anti-cancer agent comprises docetaxel, and the second anti-cancer agent comprises combretastatin.

10. The polymer-drug conjugate of claim 8, wherein the first anti-cancer agent comprises docetaxel and the second anti-cancer agent comprises gemcitabine.

11. The polymer-drug conjugate of claim 1 for use as a medicament for therapeutic therapy of cancer.

* * * * *